United States Patent [19]

Vila et al.

[11] Patent Number: 5,706,942
[45] Date of Patent: Jan. 13, 1998

[54] SURGICAL BLADE DISPENSER AND DISPOSAL APPARATUS

[76] Inventors: Raul I. Vila, 19330 E. Oakmont Dr.; Oscar Galvis, 19211 E. Oakmont Dr., both of Miami, Fla. 33015

[21] Appl. No.: 607,207

[22] Filed: Feb. 26, 1996

[51] Int. Cl.[6] .................................................. A65D 83/10
[52] U.S. Cl. .................................... 206/356; 206/359
[58] Field of Search ................................ 206/359, 352, 206/354, 355, 356, 360; 220/910; 30/40

[56] References Cited

U.S. PATENT DOCUMENTS

| | | | |
|---|---|---|---|
| 2,976,986 | 4/1961 | Linn | 206/356 |
| 3,002,607 | 10/1961 | Laverty. | |
| 4,106,620 | 8/1978 | Brimmer et al. | 206/363 |
| 4,120,397 | 10/1978 | Neumann | 206/370 |
| 4,180,162 | 12/1979 | Magney | 206/363 |
| 4,378,624 | 4/1983 | Klingenberg | 29/239 |
| 4,395,807 | 8/1983 | Eldridge, Jr. et al. | 29/239 |
| 4,730,376 | 3/1988 | Yamada | 29/239 |
| 4,746,016 | 5/1988 | Pollak et al. | 206/356 |
| 4,903,390 | 2/1990 | Vidal et al. | 29/239 |
| 5,088,171 | 2/1992 | Kromer et al. | 29/239 |
| 5,096,462 | 3/1992 | Sagstetter et al. | 206/366 |
| 5,361,902 | 11/1994 | Abidin et al. | 206/370 |
| 5,363,958 | 11/1994 | Horan | 206/356 |

*Primary Examiner*—Jacob K. Ackun
*Assistant Examiner*—Anthony Stashick
*Attorney, Agent, or Firm*—Jacobson, Price, Holman & Stern, PLLC

[57] ABSTRACT

A hollow housing is provided including a top wall defining at least one upwardly opening new blade magazine receiving recess therein and a vertical slot therethrough. The housing top wall further includes a pivoted cam lever closely adjacent the slot and by which a surgical blade releasably mounted from a surgical blade support shank may be stationarily clamped relative to the top wall to enable one handed manipulation of the support shank in a manner to disengage the latter from the surgical blade.

13 Claims, 4 Drawing Sheets

SURGICAL BLADE DISPENSER AND DISPOSAL APPARATUS

BACKGROUND OF THE INVENTION

FIELD OF THE INVENTION

This invention relates to a hollow housing including structure for supporting new, unused scalpel blades therefrom and also structure for removing used scalpel blades from a scalpel handle shank as well as a substantially fully closed storage chamber in which to contain used scalpel blades after they have been removed. The blade removable structure is in operative association with a used blade receiving opening formed in the top of the housing and a used blade to be removed from a scalpel handle shank is initially positioned within the opening in a manner such that when removal of a used blade is effected, the used blade is free to fall by gravity into the interior of the housing.

DESCRIPTION OF RELATED ART

Various different forms of surgical blade dispensers and disposal devices heretofore have been provided such as those disclosed in U.S. Pat. Nos. 3,002,607, 4,106,620, 4,120,397, 4,180,162, 4,395,807, 4,730,376, 4,746,016, 4,903,390, 5,088,173 and 5,361,902.

While these previously known apparatuses include some of the general structural and operational features of the instant invention, the specific blade removal structure of the instant invention enabling a one handed blade removal operation and the specific new blade support structure enabling a one handed new blade attachment operation are not disclosed by the above mentioned prior art references.

SUMMARY OF THE INVENTION

The surgical blade dispenser and disposal apparatus of the instant invention is in the form of a hollow housing including a top wall. The top wall includes blade support structure for supporting a plurality of new surgical blades therefrom in position to be operationally engaged by the shank of a scalpel handle through utilization of a one handed operation. The top wall further includes an opening formed therethrough for entrance of used blades by gravity into an interior used blade storage compartment within the housing and the top wall of the housing also includes blade removal structure, in operative association with the blade receiving opening, for effecting blade removal from a scalpel handle shank through utilization of a one handed operation.

By providing a surgical blade dispenser and disposal apparatus of this type a person conducting an autopsy may quickly and conveniently change surgical blades with his or her hand and fingers spaced at least one inch remote from the cutting edge of a used blade being discarded or a new blade being attached to the scalpel shank.

The main object of this invention is to provide a surgical blade dispenser and disposal apparatus defining a receptacle for used scalpel blades.

Another object of this invention is to provide a used blade receptacle including used blade removal structure.

Yet another object of this invention is to provide a used blade receptacle for containing used blades in a safe and fully enclosed manner.

A further object of this invention is to provide a receptacle for used blades including used blade removal structure and also provided with new blade support structure enabling a scalpel handle blade shank to be operatively engaged with a new blade and utilized to remove the new blade from the blade support structure through utilization of a one handed operation.

A still further object of this invention is to provide a receptacle for used blades operative to effectively remove a scalpel blade from a scalpel handle shank through utilization of a one hand operation.

A final object of this invention to be specifically enumerated herein is to provide a surgical blade dispenser and disposal apparatus in accordance with the preceding objects and which will conform to conventional forms of manufacture, be of simple construction and easy to use so as to provide a device that will be economically feasible, long lasting and relatively trouble free in operation.

These together with other objects and advantages which will become subsequentially apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
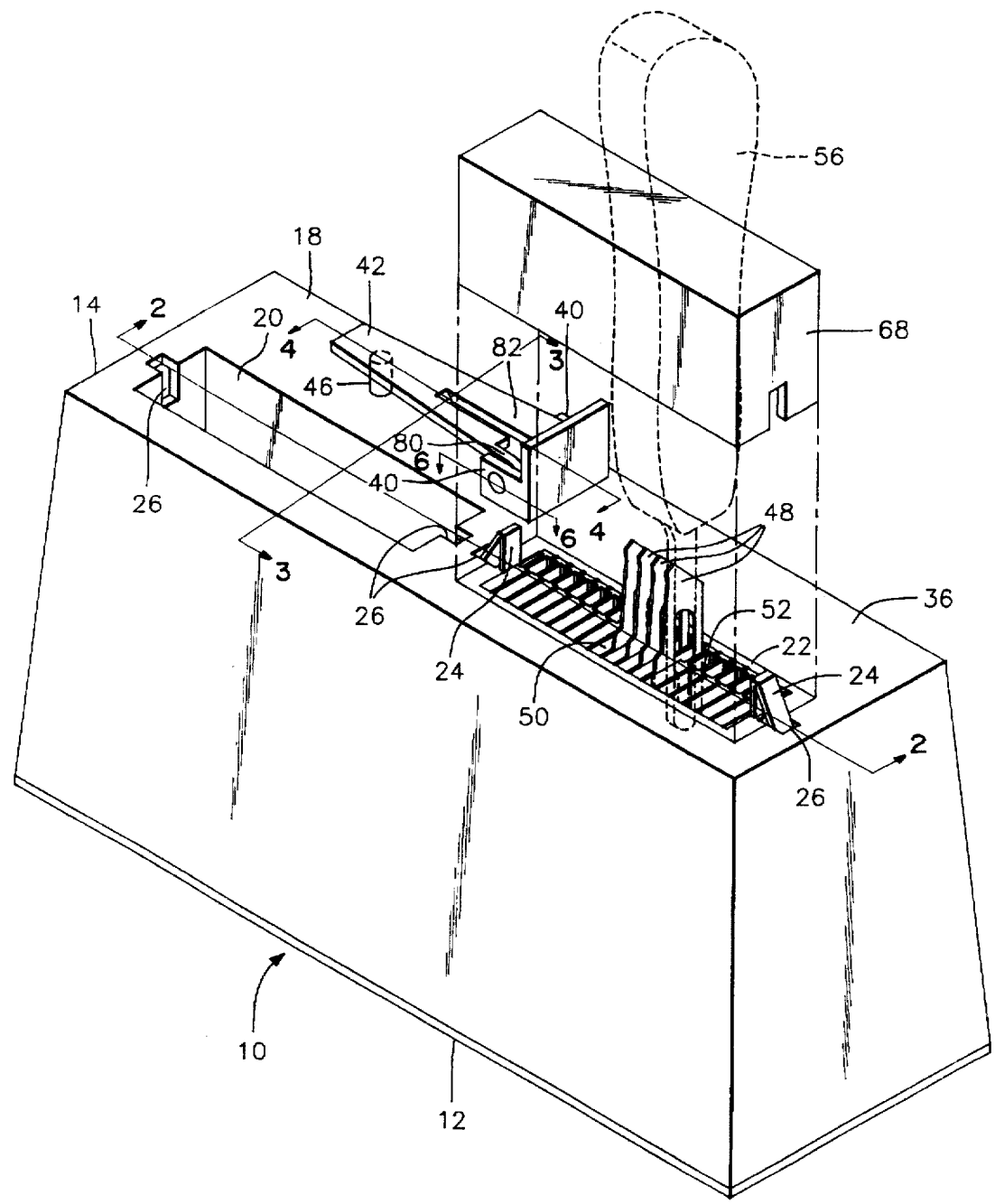
FIG. 1 is a perspective view of the combined dispenser and disposal apparatus of the instant invention and illustrating one new blade magazine removably supported in one of the two magazine receiving recesses formed in the removable top of the apparatus and with a removable cover for the blade magazine illustrated in exploded position, a surgical knife handle and shank being illustrated in phantom lines in position for removable engagement with a new surgical blade.

Referring now more specifically to the drawings the numeral 10 generally designates the surgical blade dispenser and disposal apparatus of the instant invention. The apparatus 10 includes a base 12 downwardly over which a downwardly opening cover or housing 14 is removably positionable, the base 12 including 90° angularly displaceable latches 16 for removably securing the cover or housing 14 to the base 12.

The combination of the base 12 and the housing 14 defines a hollow receptacle including a first wall 18 comprising the top wall of the housing 14 and defining a pair of upwardly opening recesses 20 in which surgical blade magazines 22 are receivable, the magazines 22 including yieldable latches 24 cooperating with extensions 26 of the recesses 20 for releasably securing the magazines 22 within the recesses 20.

Figure 2:
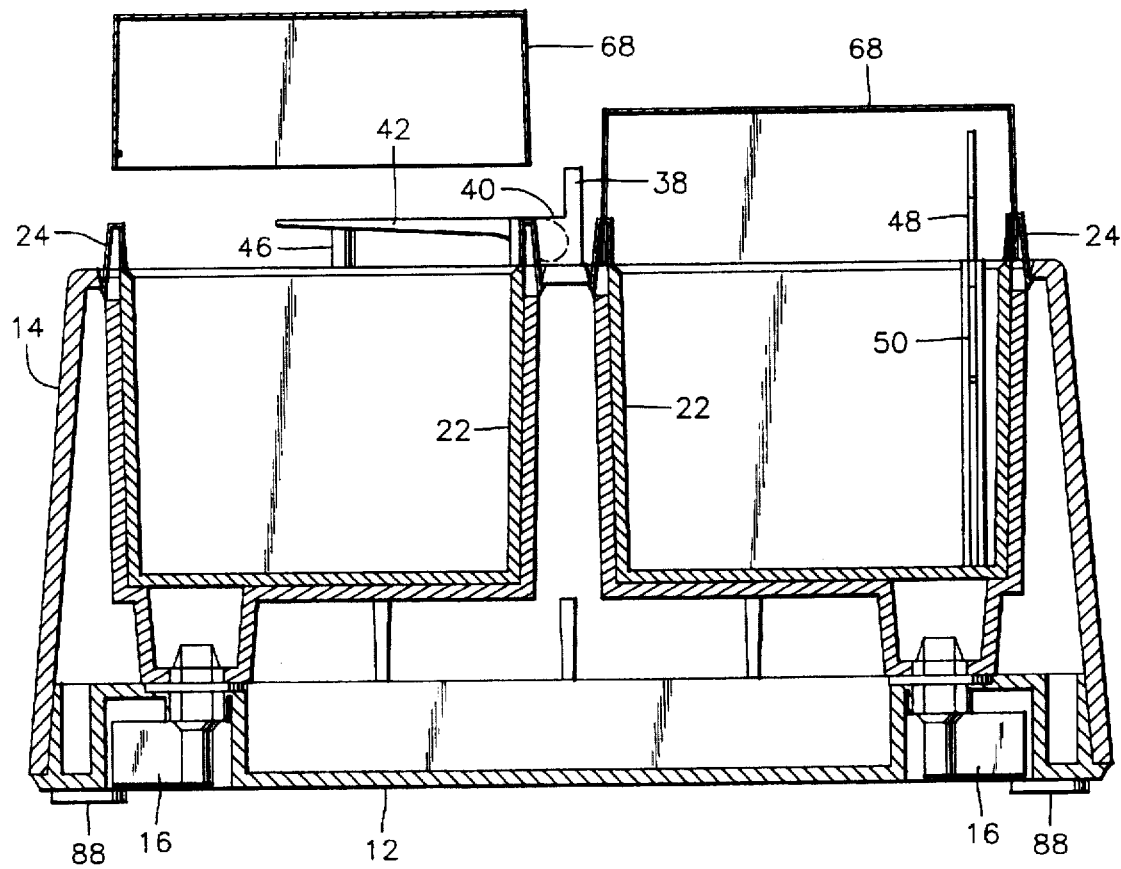
FIG. 2 is a longitudinal vertical sectional view of the blade dispenser and disposal apparatus taken substantially upon a plane indicated by the section line 2—2 of FIG. 1 illustrating one new blade support structure of one of the new blade magazines shown in elevation and the cover of the second new blade magazine illustrated in exploded position.
Figure 5:
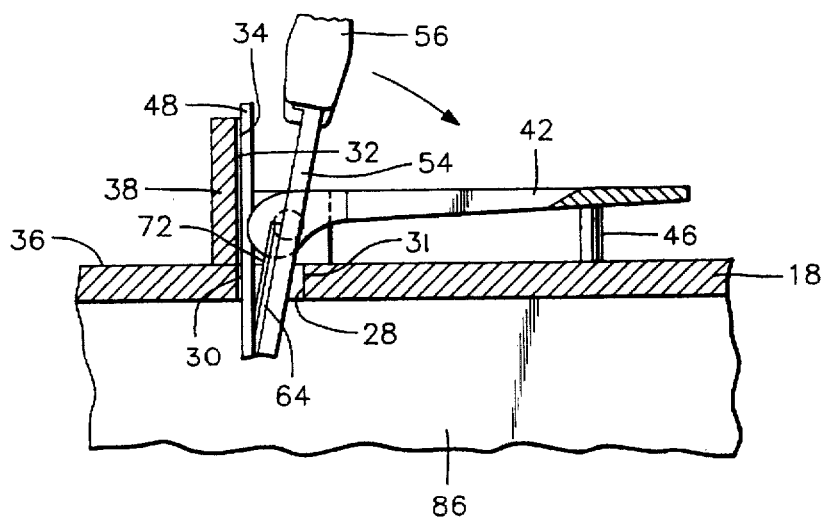
FIG. 5 is an enlarged fragmentary vertical sectional view similar to FIG. 4 but illustrating the used blade in its initial clamped disposal position and with the surgical blade handle and support shank angularly displaced to a blade release position immediately prior to upward disengagement of the support shank from the used blade and counterclockwise angular displacement of the cam lever to a release position for gravity release of the used surgical blade down into the used blade compartment of the dispenser and disposal apparatus.

The first or top wall 18 also has a vertical slot 28 formed therein defining a pair of opposite sides 30 and 31. The side 30 includes a vertical notch 32 defining a pair of laterally spaced abutments 34 extending outwardly of the outer side 36 of the first or top wall 18 with the spacing between the laterally spaced abutments 34 registered with the notch 32. The abutments 34 comprise horizontally laterally spaced vertical ridges defined on an abutment plate 38 projecting upwardly and outwardly of the outer side 36 of the first or top wall 18 and opposite side margins of the abutment plate 38 include horizontally directed and laterally spaced apart mounting flanges 40 between which a bifurcated cam lever 42 is pivotally mounted as at 44. The lever 42 is swingable between an inoperative substantially vertical position and the operative horizontal position thereof illustrated in FIGS. 2 and 5 abutted against an upwardly projecting stop pin 46 carried by and projecting upwardly from the first or top wall 18.

Figure 3:
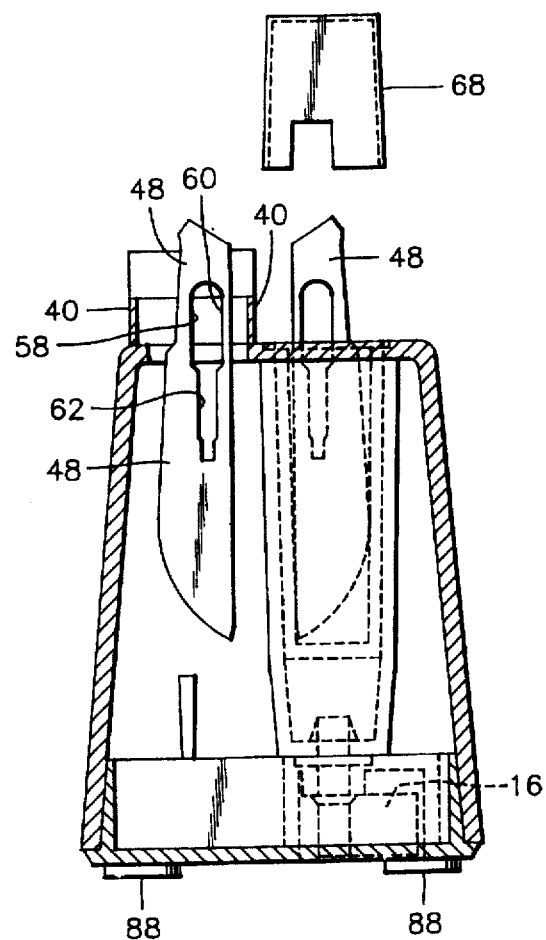
FIG. 3 is a transverse vertical sectional view of the surgical blade dispenser and disposal apparatus taken substantially upon a plane indicated by the section line 3—3 of FIG. 1 and passing through the used blade receiving opening formed in the top wall of the blade dispenser and disposal apparatus.

With attention now invited more specifically to FIGS. 1 and 3 of the drawings, it may be seen that a plurality of surgical blades 48 may be carried in each magazine 22, the blades 48 each being received in an individual upstanding and upwardly opening slot 50 defined by the corresponding magazine 22. Each surgical blade receiving slot 50 includes an enlarged portion 52 defining an area of greater width of the slot and the blade mounting shank 54 of a surgical blade handle 56 is downwardly receivable in each enlarged portion 52 along side the corresponding surgical blade 48. The surgical blades 48 are of conventional design and include a longitudinal slot 58 including greater and smaller dimension ends 60 and 62. The mounting shank 54 is conventional in design and includes narrow opposite side grooves 64, see FIG. 5, in which those portions of the corresponding blade 48 disposed on opposite sides of the small dimension end 62 of the slot 58 engage, this cooperating structure of the mounting shank 54 and blades 48 being old and well known.

Each of the magazines 22 includes a removable downwardly opening cover 68 therefor to protect the blades 48 and when a new blade 48 is required, the corresponding cover is lifted and the shank 54, supported from the handle 56, is downwardly inserted into the corresponding enlarged portion 52 with the shank 54 slightly inclined downwardly toward the blade 48 to be engaged. The free end of the shank 54 is then engaged with those portions of the blade defining the opposite sides of the small dimension end 62, which blade portions are received in the grooves 64. As downward movement of the shank 54 continues the blade 48 flexes until the upper end of the greater dimension end 60 registers with the upper end 70 of the laterally enlarged portion 72 of the shank 54 in which the grooves 64 are formed. At this point, the resiliency of the blade 48 snaps the upper end of the blade 48 into engagement with the upper side surface 76 of the mounting shank 54 above the enlarged portion 72 to thus lock the blade 48 to the mounting shank 54. Thereafter, the handle 56 is upwardly displaced to withdraw the mounting shank 54 and the attached new blade 48 from the associated slot 50 of the magazine 22.

Figure 4:
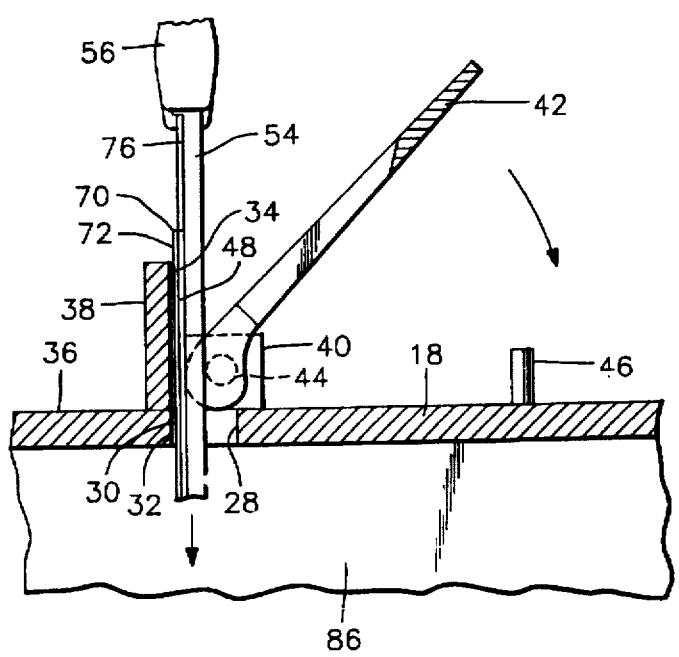
FIG. 4 is an enlarged fragmentary vertical sectional view taken substantially upon a plane indicated by the section line 4—4 of FIG.1 illustrating the manner in which a used surgical blade is downwardly inserted into the used blade receiving opening at the beginning of a blade disposal operation.
Figure 6:
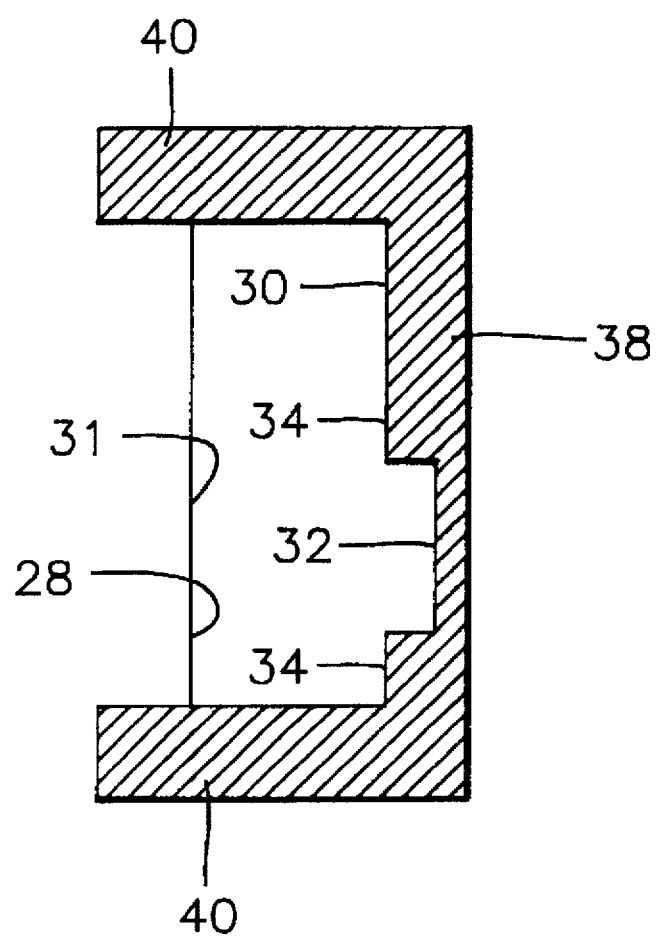
FIG. 6 is an enlarged horizontal sectional view taken substantially upon a plane indicated by the section line 6—6 of FIG. 1.

When it is desired, on the other hand, to remove a used blade 48 from the mounting shank 54, the handle 56 is used to insert the mounting shank 54 and the used blade 48 down into the slot 28. The initial positioning of the shank 54 and blade 48 in the slot 28 is illustrated in FIG. 4 of the drawings with the lever 42 in the position thereof illustrated in FIG. 4 and the laterally enlarged portion 72 of the shank 54 received in the notch 32. Thereafter, the handle 56 is further displaced downwardly from the position thereof illustrated in FIG. 4 until the lower end of the handle 56 abuts the upper end of the abutment plate 38 and/or one of the flanges 40. Thereafter, the free end of the cam lever 42 is swung downwardly from the position thereof illustrated in FIG. 4 toward the position illustrated in FIG. 5 in order to tightly clamp the blade 48 against the abutments 34, the cam end of the lever 42 being bifurcated to include bifurcations 80 and 82, see FIG. 1, which bifurcations are registered with the abutments 34 with the spacing between the bifurcations 80 and 82 being registered with the notch 32.

The pivoted end of the lever 42 thus tightly clamps those portions of the blade 48 on opposite sides of the small dimension end 62 of the slot 58 against the abutments 34. At this point, the handle 56 is laterally displaced to the right as viewed in FIG. 4 to generally the position thereof illustrated in FIG. 5, whereupon the lower end of the blade 48 is flexed and the upper end of the enlarged portion 72 is laterally displaced outwardly of the greater dimension end 60 of the slot 58. Thereafter, an upward force is applied to the handle 56 in order to upwardly withdraw the latter and thus the lower end portion of the slotted enlarged portion 72 upwardly from engagement with the blade 48. This of course completely disengages the mounting shank 54 from the used blade 48. After upward withdrawal of the mounting shank 54 from the slot 28 has been completed, the free end of the lever 42 may be swung upwardly from the position thereof illustrated in FIG. 5 to the position illustrated in FIG. 4 whereupon the used blade 48 projecting through the slot 28 will be released for falling by gravity downwardly through the slot 28 and into the used blade receiving chamber 86 defined within the interior of the housing 14.

Of course, if a new blade 48 is desired on the shank 54, a new blade from the magazine 22 is selected and the mounting shank 54 is engaged therewith in the manner hereinabove set forth.

The underside of the base 12 is provided with resilient feet 88 for support from any suitable supporting surface and, if desired, such supporting surface may include suction cups (or suction cups may be provided on the bottom of the base 12) for releasably securely fastening the base 12 to a suitable support surface. In this case, the mounting of a new blade on the mounting shank 54 may be accomplished by a one hand operation and the removal of a used blade 48 from the mounting shank 54 also may be accomplished through utilization of a one handed operation. Such operation will of course be of great benefit to a single person conducting an autopsy.

The foregoing is considered as illustrative only of the principles of the invention. Further, since numerous modifications and changes readily will occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A surgical blade disposal apparatus including a hollow receptacle defined in part by a first wall having inner and outer sides, said first wall having a slot formed therein defining a pair of opposite sides, one of said opposite sides including a notch therein, said receptacle defining laterally spaced abutments extending outwardly of said outer side at opposite end portions of said one side of said slot, and laterally spaced clamp structure shiftably supported from said first wall outwardly of said outer side and including laterally spaced clamp surfaces opposing and registered with said abutments, said clamp surfaces being movable toward and away from said abutments for clamping against and releasing from said abutments, respectively, a longitudinally slotted blade extending through said slot with the slot of said blade registered with said notch.

2. The apparatus of claim 1 wherein said receptacle includes a base and a hollow, downwardly opening cover removably secured to said base, of said cover, said first wall comprising a top wall.

3. The apparatus of claim 1 wherein said clamp structure comprises a rotary cam mounted from said first wall for angular displacement relative thereto.

4. The apparatus of claim 2 wherein said cover top wall defines at least one deep, upwardly opening recess therein, and an upwardly opening compartmented surgical blade magazine removably received in said recess.

5. The apparatus of claim 4 wherein said compartmented surgical blade magazine includes support structure for supporting heel end upstanding surgical blades therein in laterally spaced relation with said heel ends projecting outwardly of said support structure.

6. The apparatus of claim 2 wherein said base includes underside accessible latch structure shiftable between unlatched and latched positions for releasably latching said cover to said base.

7. The apparatus of claim 1 wherein said abutments include outer ends projecting outwardly of said first wall a distance sufficient to abut a handle of a surgical knife blade support shank projecting inward through said slot in registry with said notch when said handle is spaced slightly outwardly of said first wall.

8. The apparatus of claim 7 wherein said receptacle includes a base and a hollow, downwardly opening cover removably secured to said base, said first wall comprising a top wall.

9. The apparatus of claim 8 wherein said clamp structure comprises a rotary cam mounted from said first wall for angular displacement relative thereto.

10. The apparatus of claim 9 wherein said cover top wall defines at least one deep, upwardly opening recess therein, and an upwardly opening compartmented surgical blade magazine removably received in said recess.

11. A surgical blade disposal apparatus including a first wall having inner and outer sides, said first wall having a slot formed therein defining a pair of opposite sides, one of said opposite sides including a notch therein, said apparatus defining laterally spaced abutments extending outwardly of said outer side at opposite end portions of said one side of said slot, and laterally spaced clamp structure shiftably supported from said first wall outwardly of said outer side and including laterally spaced clamp surfaces opposing and registered with said abutments, said clamp surfaces being movable toward and away from said abutments for clamping against and releasing from said abutments, respectively, a longitudinally slotted blade extending through said slot with the slot of said blade registered with said notch.

12. The surgical blade disposal apparatus of claim 11 wherein said clamp structure comprises a rotary cam mounted from said first wall for angular displacement relative thereto.

13. The surgical blade disposal apparatus of claim 12 wherein said rotary cam includes a pair of laterally spaced bifurcations carried by one end of an elongated lever pivotally mounted from said first wall.

* * * * *